United States Patent [19]

Wachholz et al.

[11] Patent Number: 5,105,030
[45] Date of Patent: Apr. 14, 1992

[54] METHOD OF MANUFACTURING DIHYDROMYRCENOL FROM DIHYDROMYRCENYL CHLORIDE

[75] Inventors: Gerhard Wachholz, Marl; Heinz-Werner Voges, Dorsten, both of Fed. Rep. of Germany

[73] Assignee: Huels Aktiengesellschaft, Marl, Fed. Rep. of Germany

[21] Appl. No.: 713,562

[22] Filed: Jun. 11, 1991

[30] Foreign Application Priority Data

Jul. 6, 1990 [DE] Fed. Rep. of Germany ....... 4021578

[51] Int. Cl.$^5$ .......................................... C07C 29/124
[52] U.S. Cl. ................................... 568/894; 568/840; 568/891; 568/892; 568/893
[58] Field of Search ............... 568/825, 827, 840, 891, 568/892, 893, 894

[56] References Cited

U.S. PATENT DOCUMENTS

| 2,819,319 | 7/1958 | Barnes | 568/894 |
| 3,157,705 | 11/1964 | Pearce | 568/894 |
| 4,791,222 | 12/1988 | Sprecker et al. | 568/893 |

FOREIGN PATENT DOCUMENTS

| 0078134 | 5/1984 | Japan | 568/892 |
| 1008206 | 3/1983 | U.S.S.R. | 568/892 |

Primary Examiner—Werren B. Lone
Attorney, Agent, or Firm—Oblon, Spivak, McClelland, Maier & Neustadt

[57] ABSTRACT

Dihydromyrcenol is prepared from dihydromyrcenyl chloride by hydrolyzing dihydromyrcenyl chloride in an aqueous medium containing a base and a phase transfer catalyst in an amount of 0.001–10 mol %, based on the amount of dihydromyrcenyl chloride.

6 Claims, No Drawings

METHOD OF MANUFACTURING DIHYDROMYRCENOL FROM DIHYDROMYRCENYL CHLORIDE

BACKGROUND OF THE INVENTION

1. Field of the Invention

The present invention relates to an improved and substantially simplified method of producing dihydromyrcenol, using dihydromyrcenyl chloride as the starting material.

2. Description of the Background

Dihydromyrcenol is a monoterpene which has many uses in the fragrance industry. Derivatives of dihydromyrcenol such as ethers and esters are particularly important.

Dihydromyrcenyl chloride is converted directly into the alcohol by hydrolysis in the presence of a basic buffer. This hydration reaction is an important partial step in the synthesis sequence from the natural material α-pinene, via cis-pinane, dihydromyrcene, and dihydromyrcenyl chloride, to the desired fragrance substance, dihydromyrcenol.

It is known, and is described in numerous publications, that one may produce dihyd omyrcenol from α-pinene using the following multistage synthesis:

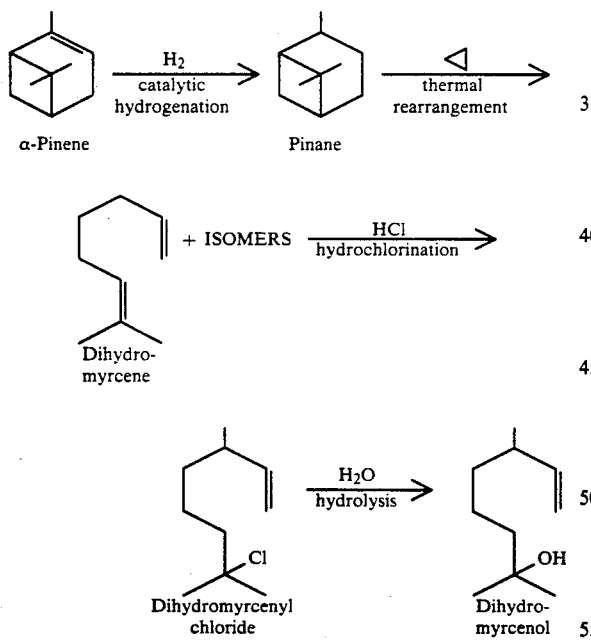

α-pinene is hydrogenated to pinane, with the cis-isomer being much more useful for the subsequent thermal rearrangement whereby the pinane can be selectively converted to dihydromyrcene. The hydrogenation is described in Cocker, W., 1966, *J. Chem. Soc.* (C), 41–47; and U.S. Pat. Nos. 4,018,842 and 4,310,714.

Cis-pinane may be rearranged thermally in the gas phase at temperatures of 420°–600 ° C., whereby dihydromyrcene may be obtained as the main product. However, a whole series of structural isomers is produced:

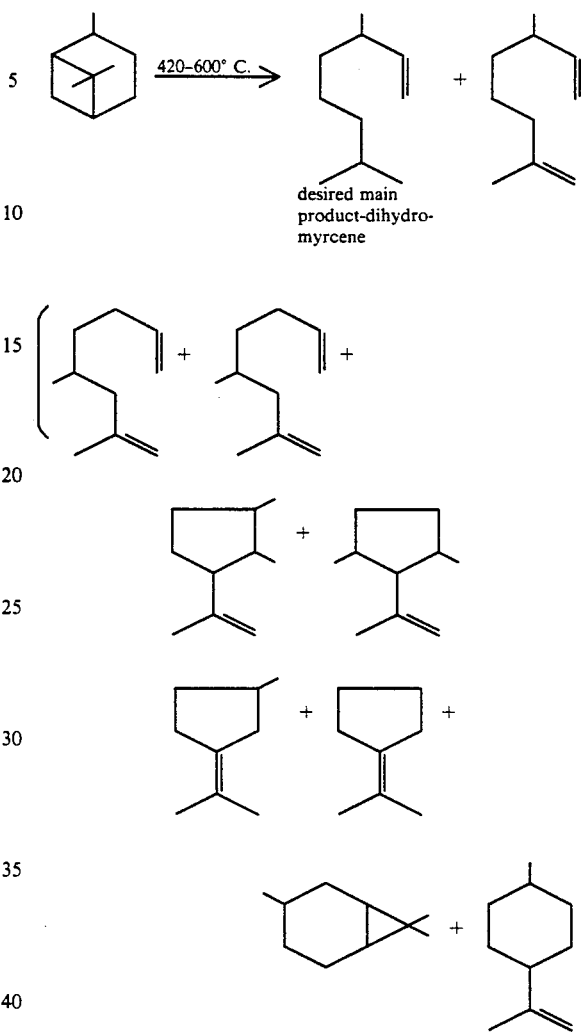

This thermal rearrangement is described in a number of patents, among them U.S. Pat. Nos. 2,388,084, 2,902,495, and 3,277,206, and Ger. Patents 1,149,000 and 2,744,386. This reaction has been much studied in the scientific literature, beginning some time ago, as illustrated by the following: Ipatieff, V.N., *JACS*, 75:6222-6225, (1953); Huntsman, W.D., *JACS*, 80:2252-2254, (1957); Pines, H., *JACS*, 76:4412-4416, (1954); and Tanaka, J., 1971, *Bull. Chem. Soc. Japan*, 44:130-132, (1971).

The production of dihydromyrcenol itself is very selective. It is produced in good yield from dihydromyrcenyl chloride and subsequent hydrolysis. Hydrochlorination of dihydromyrcene may be accomplished by introducing dry HCl gas into dihydromyrcene, as described in Brit. Patent 849,567. Various catalysts have been proposed to enhance the reaction. Examples are copper chloride (Jap. Patent 60-058,930) and Lewis and proton acids (Eur. Patent OS 0,170,205). A common feature of all of the hydrochlorination reactions is that one may use the raw product mixture of the thermal rearrangement as the starting material, or one may use pure dihydromyrcene.

In the past, the hydrolysis of the chloride obtained was carried out primarily by addition of NaOH, Ca(OH)$_2$, or CaCO$_3$ and and Na$_2$CO$_3$. These techniques are described in Brit. Patent 859,567 and U.S. Pat. No. 2,882,323. Recently, the addition of so-called hydroxylation catalysts, e.g. ZnO, has been described in detail (Eur. OS 0,170,205). In the Examples of Eur. OS 0,170,205 it is disclosed that the hydroxylation catalyst ZnO is used in the amount of 0.6 mol per 1 mol dihydromyrcenyl chloride.

The reaction steps from α-pinene to dihydromyrcenyl chloride, regarded as the State of the Art, comprise a well developed and continually improved technology. It is quite surprising, therefore, that no such highly refined method is available for the hydrolysis step, particularly since this step is the last and crucial step in the production of the desired end product, and the sequence itself is a costly one.

A major disadvantage of the present method of hydrolysis is the long duration of the hydrolysis which duration is taught in the art. For example, after 15 hr reflux dihydromyrcenyl chloride is still present in the amount of 5-10% in the reaction mixture as disclosed in Brit. Patent 859,567. In order to further reduce the residual dihydromyrcenyl chloride it is necessary to extend the hydrolysis time substantially. According to this known method, extremely long reaction times of c. 3-6 da are required to achieve a conversion such that the residual content of dihydromyrcenyl chloride is <0.1%.

Another negative aspect is the costly process which must be employed to separate the desired dihydromyrcenol from the unconverted chloride. In a recent method (Eur. 03 0,170,205) an improvement is described which is realized by the use of so-called hydroxylation reagents, e.g. zinc oxide and magnesium oxide. However, the improvement is only partial, and the hydrolysis times are still very long. In a typical example, after 11 hr under reflux the conversion of the dihydromyrcenyl chloride is only c. 70%.

The small advance represented by the teaching of Eur. OS 0,170,205 over Brit. Patent 859,567, if there is in fact any advance detectable, is nullified by the phase separation problems which occur in processing the product mixture following a successful hydrolysis. These problems are evidently caused by the large amount of zinc oxide used (>/=0.3 mol zinc oxide per 0.5 mol dihydromyrcenyl chloride), which is evidently largely converted to zinc chloride. A need therefore continues to exist for an improved technique of hydrolyzing dihydromyrcenyl chloride to dihydromyrcenol.

SUMMARY OF THE INVENTION

Accordingly, one object of the present invention is to substantially improve the very important last step in the synthesis sequence from α-pinene to dihydromyrcenol, in particular, by enabling the maximum possible degree of conversion of dihydromyrcanyl chloride to the alcohol in an appreciably shorter reaction time.

Another object is to provide an appreciably simplified distillative refinement of the reaction product dihydromyrcenol by maximizing the possible degree of conversion of dihydromyrcenyl chloride.

Still another object is to avoid phase separation problems during product processing after successful hydrolysis of dihydromyrcenyl chloride.

Briefly, these objects and other objects of the present invention as hereinafter will become more readily apparent can be attained by hydrolyzing dihydromyrcenyl chloride in an aqueous medium containing a base and a phase transfer catalyst in an amount of 0.001-10 mol%, based on the amount of dihydromyrcenyl chloride.

DETAILED DESCRIPTION OF THE PREFERRED EMBODIMENTS

A number of phase transfer catalysts have been tested for their usefulness in the hydrolysis reaction of the invention. It has been found that a relatively small amount of such materials provides a surprisingly large increase in the hydrolysis rate, as will be described in more detail hereinbelow. Suitable phase transfer catalysts include quaternary salts such as quaternary ammonium, phosphonium and pyridinium salts.

If the hydrolysis reaction is conducted in a customary fashion, e.g. by reacting dihydromyrcenyl chloride with an aqueous solution of sodium hydrogen carbonate or another basic compound, then, as described in more detail in the Comparison Example, infra, a reaction time of 22 hr must be employed under reflux conditions of about 100° C. Even after this long time, the residual content of dihydromyrcenyl chloride in the reaction mixture is 4%. The addition of only 0.5 mol%, based on the amount of dihydromyrcenyl chloride, hexadecyltrimethylammonium bromide reduces the reaction time to </=2 hr, with the residual content of the chloride being 0.5%.

Even with additions of <0.5 mol% of catalyst, residual contents of organic chloride can be achieved which are markedly less than the chloride contents encountered in the known hydrolysis processes. No phase problems occur with the use of the present method. The organic phase which contains the desired dihydromyrcenol immediately and cleanly separates out upon cooling of the reaction mixture to a temperature below the boiling point of the aqueous phase, e.g. below 100° C.

A surprising, unforeseeable fact is that if 1 mol% of a phase transfer catalyst, based on the weight of the dihydromyrcenyl chloride, is added to the reaction medium, which catalyst may be, e.g. hexadecyltrimethylammonium bromide, the dihydromyrcenyl chloride is no longer detectable after 30 hr reaction time. Another surprising, unforeseeable fact is that the hydrolysis which is accelerated by the phase transfer catalyst is not attended by any loss of selectivity.

Suitable examples of phase transfer catalysts include quaternary compounds such as various substituted phosphonium-, ammonium-, and pyridinium halides. Specific examples include, e.g., tetrabutylammonium halides, tetrabutylphosphonium halides, hexadecylpyridinium halides, and hexadecyltrimethylammonium halides. Suitable organic substituents include tetraethyl, alkyltriethyl, phenyl, benzyl, n-octyltrimethyl, tetrabutyl, and the like groups. The halides used are papticularly bromide and chloride. A preferred catalyst is hexadecyltrimethylammonium halide, particularly the bromide.

It should be emphasized that the phase transfer catalysts employed may be reused, with the effect of substantially reducing the amount of waste water.

The mol% of the phase transfer catalyst employed, based on the amount of dihydromyrcenyl chloride, may be 0.001-10 mol%, preferably 0.05-1 mol%.

The amount of water in the reaction system, based on the amount of dihydromyrcenyl chloride, may be 1-100 mol-equivalents. The hydrolysis is carried out at 10°-100° C. at normal pressure, preferably 90°-100° C.

The amount of basic buffer added per mol of dihydromyrcenyl chloride should be between 1.0 and 5 mol, preferably 1–1.25 mol.

There are mo limitations on the base employed, but it has been found that the weaker the base the lower the amount of elimination products. Suitable bases include especially NaOH, KOH, Ca(OH)$_2$, NaHCO$_3$, Na$_2$CO$_3$, Li$_2$CO$_3$, LiHCO$_3$, and KHCO$_3$, preferably NaHCO$_3$.

The dihydromyrcenyl chloride employed may be the pure substance or a mixture comprised of various terpenoid chlorides. Such mixtures do not present problems of selectivity with regard to the dihydromyrcenol.

The advantages to be achieved by the technique of the invention particularly include the following:
(i) Substantial shortening of the reaction time may be achieved.
(ii) Very little phase transfer catalyst is required.
(iii) There are no phase separation problems.
(iv) Mixtures of various terpenoid chlorides.

Dihydromyrcenol is useful as a fragrance

Having general described this invention, a further understanding can be obtained by reference to certain specific examples which are provided herein for purposes of illustration only and are not intended to be limiting unless otherwise specified.

COMPARISON EXAMPLE

Into a 250 ml three-necked flask equipped with a stirrer, thermometer, and reflux condenser, 27 g of a dihydromyrcenyl chloride mixture comprised of 90%=24.3 g=0.14 mol of dihydromyrcenyl chloride and 10% =2.7 g=0.02 mol dehydromyrcene, 8 g (0.2 mol) NaOH, and 108 ml (6 mol) H$_2$O were charged. The solution was heated to boiling 22 hr under reflux. Then the organic phase was separated, washed with water, and dried. 56% dihydromyrcenol, 4% dihydromyrcenyl chloride, and 40% dihydromyrcene were obtained.

Then the reaction mixture was distilled through a packed column, under a vacuum, from the dihydromyrcene.

EXAMPLE 1

The procedure described in the Comparative Example was employed except that 11.8 g (0.14 mol) NaHCO$_3$, and 0.68 mmol (0.25 g) hexadecyltrimethylammonium bromide (cetyltrimethylammonium bromide) were added to the flask. After 2 hr of reflux the organic phase contained 64% dihydromyrcenol, 0.5% dihydromyrcenyl chloride, and 33.5% dihydromyrcene. The addition of the phase transfer catalyst resulted in a more than tenfold reduction in reaction time, accompanied by a modest improvement in selectivity.

EXAMPLE 2

The procedure described in Example 1 was employed, except that 0.68 mmol (0.25 g) hexadecyltrimethylammonium bromide was added to the flask. After 7 hr reflux, the organic phase contained 64.5% dihydromyrcenol, 1.0% dihydromyrcenyl chloride, and 34.5% dihydromyrcene. The addition of as little as <0.05 mol%, based on the chloride, brought about a substantial reduction in the reaction time.

EXAMPLE 3

The procedure described in Example 1 was employed except that 2.85 mmol (0.91 g) hexadecyltrimethylammonium chloride was added. After 30 hr reflux, the organic phase contained 62% dihydromyrcenol and 38% dihydromyrcene. Under these reaction conditions dihydromyrcenyl chloride was no longer detectable.

EXAMPLE 4

The procedure described in Example 1 was employed except that 0.2 mmol (0.06 g) hexadecylpyridinium bromide was added to the flask. After 3 hr reflux, the organic phase contained 65% dihydromyrcenol, 1.5% dihydromyrcenyl chloride, and 33.5% dihydromyrcene.

EXAMPLE 5

The procedure described in Example 1 was employed except that 7.3 mmol (2.8 g) hexadecylpyridinium bromide was added to the flask. After 2 hr reflux, the organic phase contained 62% dihydromyrcenol, 0.2% dihydromyrcenyl chloride, and 37.8% dihydromyrcene.

EXAMPLE 6

The procedure described in Example 1 was employed except that 13.6 mmol (4.4 g) tetrabutylammonium bromide was added to the flask. After 6 hr reflux, the organic phase contained 70.0% dihydromyrcenol, 1% dihydromyrcenyl chloride, and 29% dihydromyrcene.

EXAMPLE 7

The procedure described in Example 1 was employed except that 6.9 mmol (2.36 g) tetrabutylphosphonium bromide was added to the flask. After 6 hr the organic phase contained 61% dihydromyrcenol, 1.5% dihydromyrcenyl chloride, and 37.5% dihydromyrcene.

EXAMPLE 8

The procedure described in Example 1 was employed except that 6.2 mmol (2.8 g) methyltrioctylammonium bromide was added to the flask. After 6 hr reflux, the organic phase contained 51% dihydromyrcenol, 0.5% dihydromyrcenyl chloride, and 48.5% dihydromyrcene.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the U.S. is:

1. A method of producing dihydromyrcenol from dihydromyrcenyl chloride, comprising:
hydrolyzing dihydromyrcenyl chloride in an aqueous medium containing a base and a phase transfer catalyst in an amount of 0.001–10 mol%, based on the amount of dihydromyrcenyl chloride.

2. The method according to claim 1, wherein said phase transfer catalyst is a substituted quaternary ammonium, phosphonium-, or pyridinium halide.

3. The method according to claim 2, wherein said phase transfer catalyst is a hexadecyltrimethylammonium halide.

4. The method according to claim 1, wherein the temperature of hydrolysis is 10°–100° C.

5. The method according to claim 1, wherein the hydrolysis medium contains a basic buffer in an amount of 1.0 to 5 mole per mole of dihydromyrcenyl chloride.

6. The method according to claim 1, wherein said base is NaOH, KOH, Ca(OH)$_2$, NaHCO$_3$, Na$_2$CO$_3$, Li$_2$CO$_3$ or LiHCO$_3$.

* * * * *